(12) United States Patent
Olson

(10) Patent No.: US 10,155,107 B2
(45) Date of Patent: Dec. 18, 2018

(54) IMPLANTABLE MODULAR ELECTRODE ARRAY ASSEMBLY

(71) Applicant: Medtronic, Inc., Minneapolis, MN (US)

(72) Inventor: Robert L. Olson, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/285,817

(22) Filed: Oct. 5, 2016

(65) Prior Publication Data

US 2017/0100580 A1 Apr. 13, 2017

Related U.S. Application Data

(60) Provisional application No. 62/238,524, filed on Oct. 7, 2015.

(51) Int. Cl.
| | | |
|---|---|---|
| *A61N 1/00* | (2006.01) | |
| *A61N 1/05* | (2006.01) | |
| *A61B 5/0478* | (2006.01) | |
| *A61N 1/375* | (2006.01) | |
| *H01R 31/00* | (2006.01) | |

(Continued)

(52) U.S. Cl.
CPC .......... *A61N 1/0529* (2013.01); *A61B 5/0478* (2013.01); *A61N 1/0531* (2013.01); *A61N 1/0551* (2013.01); *A61N 1/375* (2013.01); *H01R 31/005* (2013.01); *A61N 1/372* (2013.01);

(Continued)

(58) Field of Classification Search
USPC .................................................. 607/46, 116
See application file for complete search history.

(56) References Cited

U.S. PATENT DOCUMENTS 3,724,467 A   4/1973 Avery et al.
4,850,359 A   7/1989 Putz
(Continued)

FOREIGN PATENT DOCUMENTS

EP   1985579 A2   10/2008
EP   2745873 A1   6/2014
(Continued)

OTHER PUBLICATIONS

International Search Report and Written Opinion from International Application No. PCT/US2016/055687, dated Apr. 4, 2017, 20 pp.
(Continued)

*Primary Examiner* — Nicole F Johnson
(74) *Attorney, Agent, or Firm* — Shumaker & Sieffert, P.A.

(57) ABSTRACT

This disclosure describes various modular electrode assemblies. For example, an implantable modular electrode assembly may include a hub including a plurality of electrical contacts configured to receive electrical signals from an implantable medical device, a first electrode module including a first substrate and a first plurality of electrodes on the first substrate, and a second electrode module including a second substrate and a second plurality of electrodes on the second substrate. The first and second electrode modules may be connectable to the hub, where the plurality of electrical contacts electrically communicate with the first and second plurality of electrodes.

16 Claims, 10 Drawing Sheets

(51) Int. Cl.
  *A61N 1/372* (2006.01)
  *H01R 12/79* (2011.01)
  *H01R 24/60* (2011.01)

(52) U.S. Cl.
  CPC .............. *H01R 12/79* (2013.01); *H01R 24/60* (2013.01); *H01R 2201/12* (2013.01)

(56) References Cited

U.S. PATENT DOCUMENTS

| | | |
|---|---|---|
| 5,417,719 A | 5/1995 | Hull et al. |
| 6,038,480 A | 3/2000 | Hrdlicka et al. |
| 6,597,953 B2 | 7/2003 | Boling |
| 7,107,104 B2 | 9/2006 | Keravel et al. |
| 7,305,268 B2 | 12/2007 | Gliner et al. |
| 7,715,924 B2 | 5/2010 | Rezai et al. |
| 7,818,063 B2 | 10/2010 | Wallace et al. |
| 7,941,202 B2 | 5/2011 | Hetke et al. |
| 8,090,446 B2 | 1/2012 | Fowler et al. |
| 8,126,568 B2 | 2/2012 | Gliner |
| 8,185,208 B2 | 5/2012 | Garabedian et al. |
| 8,359,107 B2 | 1/2013 | Pianca et al. |
| 8,478,423 B2 | 7/2013 | McDonald et al. |
| 8,594,778 B2 | 11/2013 | VanSickle et al. |
| 2005/0070971 A1 | 3/2005 | Fowler et al. |
| 2005/0203599 A1 | 9/2005 | Garabedian et al. |
| 2010/0145176 A1 | 6/2010 | Himes |
| 2011/0098782 A1* | 4/2011 | Kast .................... A61N 1/0529 607/46 |
| 2011/0237921 A1 | 9/2011 | Askin, III et al. |

FOREIGN PATENT DOCUMENTS

| | | |
|---|---|---|
| WO | 2009148937 A1 | 12/2009 |
| WO | 2015123255 A1 | 8/2015 |

OTHER PUBLICATIONS

Child, et al., "Chronic subthreshold subdural cortical stimulation for the treatment of focal epilepsy originating from eloquent cortex," Cortical Stimulation in Focal Epilepsy, Epilepsia, 55(3) e18-e21; Feb. 2014, 4 pp.

* cited by examiner

IMPLANTABLE MODULAR ELECTRODE ARRAY ASSEMBLY

This application claims the benefit of U.S. Provisional Application No. 62/238,524 filed Oct. 7, 2015, the entire content of which is incorporated herein by reference.

TECHNICAL FIELD

The disclosure relates to implantable systems for delivering electrical stimulation and/or sensing electrical signals.

BACKGROUND

Implantable medical devices may be configured to deliver electrical stimulation therapy and/or monitor physiological signals. Electrical stimulation of neural tissue, for example, may provide relief for a variety of disorders, improving the quality of life for many patients. Some implantable medical devices may employ elongated electrical leads that carry electrodes. For example, electrodes may be located at a distal portion of a lead. A proximal portion of the lead may include electrical contacts that are coupled to the electrodes and coupled to terminal in an implantable medical device housing, which may contain electronic circuitry such as electrical stimulation generation circuitry and/or sensing circuitry. In some examples, stimulation may be conducted using multiple electrodes and multiple stimulation leads in order to provide electrical stimulation at multiple positions within the patient or to provide electrical stimulation to a targeted area.

SUMMARY

Examples according to this disclosure are directed to a modular electrode assembly including a plurality of electrodes that may be connected to an implantable medical device designed to deliver electrical stimulation to target treatment areas within a patient. The modular electrode assembly may include a hub and one or more electrode modules that carry electrodes and mate with the hub.

In some examples, the disclosure describes an implantable modular electrode assembly that includes a hub comprising a plurality of electrical contacts, where the hub is configured to receive electrical signals from an implantable medical device, a first electrode module including a first substrate and a first plurality of electrodes on the first substrate, where the first electrode module is connectable to the hub, where at least some of the plurality of electrical contacts electrically communicate with the first plurality of electrodes, and a second electrode module including a second substrate and a second plurality of electrodes on the second substrate, where the second electrode module is connectable to the hub, where at least some of the plurality of electrical contacts electrically communicate with the second plurality of electrodes.

In some examples, the disclosure describes an implantable modular electrode assembly including a hub including a plurality or electrical contacts and at least one of a rail or a slot that extends along at least a portion of a perimeter of the hub, where the least one of the rail or the slot include the plurality of electrical contacts, where the plurality of electrical contacts are configured to receive electrical signals from an implantable medical device, and an electrode module including a substrate and a plurality of electrodes on the substrate, where the a electrode module is connectable to the at least one of the rail or the slot of the hub, where the plurality of electrical contacts electrically communicate with the plurality of electrodes.

In some examples, the disclosure describes an implantable modular electrode assembly including a hub including a first rail including a first plurality of electrical contacts extending along at least a first portion of a perimeter of the hub and a second rail including a second plurality of electrical contacts extending along at least a second portion of the perimeter the perimeter of the hub, where the hub is configured to receive electrical signals from an implantable medical device and transmit the signals to respective contacts of the first plurality of electrical contacts and the second plurality of electrical contacts, and a first electrode module that includes a first substrate, a first plurality of electrodes on the first substrate, and a first slot extending along at least a portion of a perimeter of the first electrode module, where the first slot is configured to receive the first rail of the hub, where the first plurality of electrical contacts electrically communicate with the first plurality of electrodes.

In some examples, the disclosure describes a method that includes implanting a hub of a modular electrode assembly in a patient, where the hub comprises a plurality of electrical contacts, where the hub is configured to receive electrical signals from an implantable medical device. The method may also include coupling a first electrode module to the hub, where the first electrode module includes a first substrate and a first plurality of electrodes on the first substrate, where at least some of the plurality of electrical contacts of the hub electrically communicate with the first plurality of electrodes. The method may also include coupling a second electrode module to the hub, where the second electrode module includes a second substrate and a second plurality of electrodes on the second substrate, where at least some of the plurality of electrical contacts of the hub electrically communicate with the second plurality of electrodes.

In some examples, the disclosure describes a system that includes an implantable medical device, at least one lead electrically connected to the implantable medical device, and a modular electrode assembly electrically connected to at least one lead. In some examples, the modular electrode assembly may include a hub having a plurality of electrical contacts, where the hub is configured to receive electrical signals from the implantable medical device, a first electrode module including a first substrate and a first plurality of electrodes on the first substrate, where the first electrode module is connectable to the hub and at least some of the plurality of electrical contacts electrically communicate with the first plurality of electrodes, and a second electrode module including a second substrate and a second plurality of electrodes on the second substrate, where the second electrode module is connectable to the hub and at least some of the plurality of electrical contacts electrically communicate with the second plurality of electrodes. In some examples, the implantable medical device is configured to transmit electrical signals through the lead to the first and second plurality of electrodes.

The details of one or more examples are set forth in the accompanying drawings and the description below. Other features, objects, and advantages of examples according to this disclosure will be apparent from the description and drawings, and from the claims.

DETAILED DESCRIPTION

Figure 1:
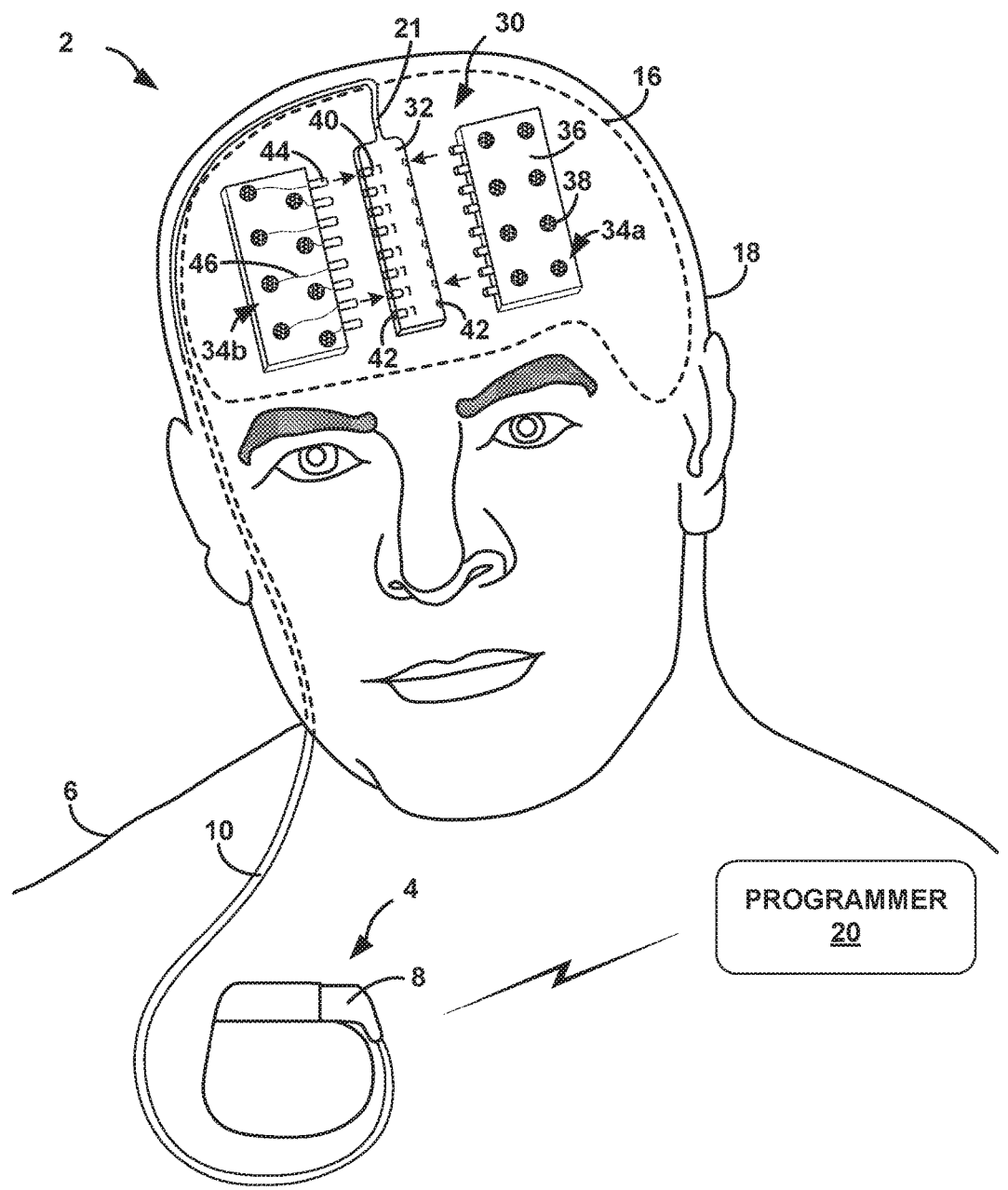
FIG. 1 is a conceptual diagram illustrating an example therapy system that includes an implantable stimulator coupled to an example modular electrode assembly.

FIG. 1 is a conceptual diagram illustrating an example system 2 that may be used to deliver stimulation therapy to patient 6. Patient 6 ordinarily, but not necessarily, will be a human. Therapy system 2 may include an implantable medical device (IMD) 4 for providing electrical stimulation to patient 6, an implantable lead 10 that transmits the electrical stimulation from IMD 4 to a modular electrode assembly 30, and a programmer 20 that programs or controls IMD 4. In some examples, lead 10 may include one or more elongated electrical conductors, each having a proximal end 8 that connects to IMD 4 and a distal end 21 that connects to modular electrode assembly 30, thereby establishing electrical communication between IMD 4 and modular electrode assembly 30. For example, a proximal end of each conductor may be connected to one of a plurality of electrical contacts, at a proximal end of lead 10, that connects to a terminal within IMD 4, and a distal end of each conductor, at a distal end 21 of lead 10, may be connected to one of a plurality of electrodes. In other examples, a proximal end of one or more conductors of lead 10 may each couple to a respective connector. Each such connector may be adapted to couple to a respective counterpart connector provided by a distal end of a lead extension (not shown). A conductor of the lead extension electrically couples the counterpart connector to a connector at the lead extension proximal end, which in turn connects to a terminal within IMD 4. Programmer 20 may be employed or implemented as either a clinician or patient programmer and may be a handheld computing device that permits users, e.g. a clinician or patient, to communicate wirelessly with IMD 4 implanted within patient 6.

As illustrated in FIG. 1, system 2 may include modular electrode assembly 30 deployed within patient 6 to provide neurological stimulation to a target treatment area. For example, modular electrode assembly 30 may be positioned near the cerebral cortex and used to deliver electrical stimulation to the cerebral cortex. Modular electrode assembly 30 may include a primary hub 32 connected to distal end 21 of lead 10. Primary hub 32 may be configured to receive at least one electrode module 34a. In the example of FIG. 1, primary hub 32 is configured to receive a first electrode module 34a and a second electrode module 34b (collectively "electrode modules 34"). In other examples, primary hub 32 may be configured to receive more than two electrode modules 34.

Electrode modules 34 may each include a substrate 36 including a plurality of electrodes 38 that form an array on the surface of the substrate 36. In some examples, the substrate 36 may be flexible, e.g., sufficiently flexible to permit the substrate to at least partially conform to an exterior surface of the cortex and/or an interior or exterior surface of the dura mater adjacent the interior surface of the cranium 18 of patient 6. Plurality of electrodes 38 may be configured to deliver electrical stimulation to target treatment areas within patient 6 (e.g., the brain 16, along the spinal cord, or the like). As one example, electrodes 38 may be configured to deliver electrical stimulation to the cerebral cortex. In some examples, multiple electrodes 38 may be used in a coordinated manner to deliver stimulation over an area of the cortex. The electrical stimulation may be supplied to electrodes 38 by implantable IMD 4 (e.g., via contacts and conductors carried by lead 10 from IMD 4 to primary hub 32, through internal circuitry of primary hub 32 to electrode modules 34, and through internal circuitry of electrode modules 34 to electrodes 38). In some examples, modular electrode assembly 30 may be implanted within patient 6 such that electrodes 38 contact brain 16. Modular electrode assembly 30 may be implanted through one or more holes in cranium 18. In some examples, the clinician may assemble modular electrode assembly 30, e.g., to primary hub 32 and first and second electrode modules 34a and 34b, before or after implanting the respective components of the assembly in the patient 6.

In some examples, modular electrode assembly 30 may be used to treat any neurological disorder for which stimulation of the cortex of brain 16 has therapeutic value. Some example neurological disorders that may be treated by modular electrode assembly 30 may include, for example, treatment of pain such as facial, neck, limbic or other pain, movement disorders such as Parkinson's disease, essential tremor and dystonia, psychological disorders such as depression and obsessive compulsive disorder (OCD), epilepsy, Huntington's Disease, and neurodegenerative disorders. In other examples, modular electrode assembly 30 may be used in other sites within a body of the patient and used to provide therapy to alleviate other symptoms and disorders.

In some examples, modular electrode assembly 30 may be placed beneath the cranium 18 of the patient either epidurally (outside the dura mater) or subdurally (beneath the dura mater). For example, in the case of treatment of pain modular electrode assembly 30 may be used epidurally. In the case of treatment of epilepsy, modular electrode assembly 30 may be used subdurally. A clinician may perform a craniotomy to implant modular electrode assembly 30 beneath cranium 18. In some examples, modular electrode assembly 30 may be placed epidurally adjacent the central sulcus of the cortex for stimulation to treat pain such as facial, neck, or limbic pain.

As shown in FIG. 1, modular electrode assembly 30 includes primary hub 32. In some examples, primary hub 32 may include a plurality of electrical contacts 40 configured to transmit electrical signals (e.g., electrical stimulation) supplied by IMD 4. For example, IMD 4 may transmit electrical signals via contacts and conductors carried by lead 10 from IMD 4 to primary hub 32. Primary hub 32 may receive the electrical signals from lead 10 and transmit the signals through internal circuitry of primary hub 32 to electrical contacts 40. The electrical signals may then be transmitted from electrical contacts 40 of primary hub 32 to one or more respective electrode module(s) 34 using a suitable configuration (the one or more electrode modules 34 are shown as electrode modules 34a and 34b in the example of FIG. 1). For example, primary hub 32 may include a plurality of ports 42 arranged along a perimeter of primary hub 32, where each port 42 includes a respective electrical contact 40. Electrode modules 34 may be configured to include a plurality of electrical connectors 44 configured to be inserted in ports 42 to both physically connect the respective electrode modules 34 to primary hub 32 as well as provide an electrical conduit from electrical contacts 40 to a respective electrode module 34. The electrical signal may then be delivered from electrical connectors 44 to a respective electrode 38 using one or more electrical conductors 46 (e.g., flex circuit, thin wires, or the like). In some examples, the plurality of ports 42 may be arranged on electrode modules 34 (not shown) such that the ports include electrical connectors 44 (e.g., in the form of a setscrew/setscrew block, a Bal Seal® terminal, or the like) and are configured to receive electrical contacts 40 of the primary hub 32.

Primary hub 32 may be formed using any suitable material. In some examples, primary hub 32 may be formed using a semi-flexible material to allow primary hub 32 to mirror, or physically conform to, the confines of the location in which primary hub 32 is implanted while maintaining sufficient rigidity to allow electrode modules 34 to be connected to primary hub 32. Suitable materials that may be used in constructing primary hub 32 may include, for example, silicone, polyurethane, or the like. In some examples, the flexible substrate may be relatively thin having a thickness of about 1.4 mm to about 2 mm, a width of about 2 mm to about 6 mm, and a length of about 40 mm to about 50 mm. Other widths and lengths of the primary hub 32 are also envisioned and may depend on the selected shape of the hub (e.g. rectangular, triangular, or the like) and the selected connector assembly with the electrode modules 34 as described further below (e.g., ports, rail/slots, or the like). In some examples, primary hub 32 may also include one or more stimulation electrodes (not shown).

Modular electrode assembly 30 also includes detachable electrode modules 34 that each include a plurality of electrodes 38 in an array on flexible substrate 36. Substrate 36 of may include any suitable flexible biocompatible materials such that electrode modules 34 may flex to contours within brain 16 of patient 6. For example, substrate 36 may include a thin sheet fabricated from a flexible material such as silicone molded, extruded, stamped, machined, or cut to a desired geometric shape. In some examples, the flexible substrate may be relatively thin (e.g., a thin film or sheet) having a thickness (e.g., as measure perpendicular to the array of electrodes 38) of less than about 2.0 mm and in some examples less than about 1.4 mm, a width of about 10 mm to about 20 mm, and a length of about 40 mm to about 50 mm to define a major surface of a single electrode module 34a having an area of about 400 mm$^2$ to about 1000 mm$^2$. Other widths and lengths of single electrode module 34a are also envisioned and may depend on the selected shape of the electrode module (e.g. rectangular, circular, or the like), the selected array of electrodes 38 (e.g., linear, grid, circular, or the like), the separation distance between adjacent electrodes 38 (e.g., between about 1.5 mm and about 20 mm), and the selected connector assembly described further below (e.g., ports, rail/slots, or the like). In some examples, a single electrode module 34a may have a major surface that defines an area less than 400 mm$^2$. In some examples, a single electrode module 34a may have a major surface that defines an area greater than 1000 mm$^2$ Electrode modules 34 may include one or more electrical conductors 46 configured to transmit an electrical signal from a respective electrical connector 44 to a respective electrode 38. Electrical conductors 46, electrical connectors 44, and/or electrodes 38 may be formed using any suitable electrically conductive material including, for example, one or more of platinum, MP35N, titanium, tantalum, niobium, and alloys thereof. In some examples, electrodes 38 may also include one or more surface coatings including, for example, Pt, TiN, IrOx, and poly(dioctylbithiophene) (PDOT) such that the surface coating lies between the electrode 38 and target treatment site.

Electrical conductors 46 may be embedded in flexible substrate 36 such that patient 6 is insulated from the transmitted electrical signal apart from the points of contact with electrodes 38. For example, electrical conductors 46 may be fabricated in the form of thin flex circuitry, conductive wire, or the like that are embedded in a silicone or other material used for form flexible substrate 36. In some examples, the various electronic components of electrode modules 34 (e.g., electrodes 38, electrical connectors 44, and electrical conductors 46) may be included integrally as part of the fabrication process of substrate 36 or may be added after the fabrication process.

As described further below, in some examples electrodes 38 may be individually activated to allow for treatment applications tailored to the specifics of patient 6. For example, all eight electrodes 38 of first electrode module 34a may be initially activated by programmer 20 to simulate a relatively large treatment area of patient 6. As treatment progresses, programmer 20 can modify the therapy to narrow the treatment area to where the stimulation is most effective (e.g., using only three of the eight electrodes 38). In other examples, initially the treatment area may be relatively small (e.g., using only one or of the eight electrodes 38) and the treatment area may be gradually expanded until the optimal stimulation is selected.

Electrodes 38 may be used to deliver electrical current in bipolar, multipolar or unipolar arrangements. For example, in a bipolar or multipolar arrangement, one or more electrodes 38 on first electrode module 34a and second electrode module 34b may be cathodes while one or more other electrodes 38 on first and second electrode modules 34a and 34b may be anodes. In some examples, the cathode and anode electrodes 38 may be present in the same electrode module (e.g., first electrode module 34a), different electrode modules (e.g., the cathode electrode in first electrode module 34a and anode electrode in second electrode module 34b or vice versa), or a combination of both. In a unipolar arrangement, one or more electrodes 38 on electrode modules 34 may be cathodes, while a housing IMD 4 may form or carry an anode. Alternatively, for a unipolar arrangement, one or more electrodes 38 on electrode modules 34 may be anodes, while a housing IMD 4 may form or carry a cathode. IMD 4 may deliver electrical stimulation via a plurality of electrodes 38 simultaneously and/or deliver stimulation at different times via different subsets of electrodes 38. The electrical stimulation may include controlled voltage pulses or controlled current pulses with amplitudes, pulse widths and pulse rates, and electrode polarities, selected to be effective for cortical stimulation to address a variety of symptoms or disorders.

In some examples, one or more of electrodes 38 may be used to detect various types of bioelectric signals, including local field potentials (LFP) of brain tissue, energy spectra in different bands, such as alpha, beta, or gamma bands of brain activity, and electrical signals associated with electrocorticography (ECoG) or electroencephalography (EEG). In one example, sense electrodes of electrode modules 34 may be employed by IMD 4 to predict the onset or detect the occurrence of a seizure related to or caused by a neurological condition of patient 6. For example, IMD 4 may be configured to employ one or more of electrodes 38 to sense one or more bioelectrical signals, e.g., LFP, ECoG, and/or EEG, in order to predict the onset or detect the occurrence of an epileptic seizure. Upon predicting or detecting the seizure, IMD 4 may deliver therapy to brain 16 of patient 6 using selected electrodes 38 to mitigate the effects of the seizure or, in some cases, prevent the onset of the seizure or manifestations of the seizure that are perceived by patient 6.

While FIG. 1 shows an example in which electrode modules 34 each include a total of 8 electrodes, in some examples, electrode modules 34 may include a greater number of electrodes or fewer number of electrodes. For example, each electrode module 34 may include between about 2 and 20 electrodes (e.g., 4, 8, or 16 electrodes). In some examples multiple electrodes 38 may be ganged together (e.g., driven by a single conductor of lead 10), powered using a multiplexing device, or the like. Electrodes 38 may be arranged in a variety of different configurations. In some examples, the plurality of electrodes 38 may be arranged in an array on the respective electrode module 34. The array may take the form of any useful configuration including, for example, a linear array (e.g., 1×8 array), or two-dimensional arrays such as a grid array (e.g., 2×8 grid (e.g., first electrode module 34a) or 4×4 grid), a staggered-array, e.g., where the rows and/or columns of electrodes are offset from adjacent rows and/or columns (e.g., where the 2×8 staggered-array of second electrode module 34b), a circular array (e.g., second electrode module 160b of FIG. 8), a combination thereof, or the like. Additionally, the specific configuration of electrode modules 34, e.g. size and shape, may vary in different examples of therapy systems according to this disclosure.

In some examples, first electrode module 34a and second electrode module 34b may be selected such that the electrode modules 34 are symmetrical or asymmetrical relative to one another. In some examples, first electrode module 34a and second electrode module 34b may be selected such that the arrays (e.g., two-dimensional arrays) of electrodes 38 on respective first electrode module 34a and second electrode module 34b for mirror images of one another to allow for symmetrical stimulation (e.g., symmetrical stimulation to the left and right hemispheres of brain 16). In some examples, the first and second electrode modules 34a, 34b need not be the same size or contain the same number of electrodes.

In some examples, the first electrode module 34a and second electrode module 34b may connect to primary hub 32 to form a substantially co-planar structure such that electrodes 38 of both electrode modules 34 are situated in substantially the same plane as one another. In other examples, electrodes 38 may lie in different planes. For instance, first electrode module 34a may connect to primary hub 32 such that a first plane in which the electrode 38 of the first electrode module 34a are situated forms an angle of less than about 180 degrees with a second plane in which electrodes 38 of second electrode module 34b are situated. In some examples, more than two such electrode modules 34 may couple to primary hub 32 via respective sets of ports 42 that are provided on more than two surfaces of primary hub 32 with less than about 180 degrees between the two electrode modules 34.

In some examples, flexible substrate 36 of an electrode modules 34 may be substantially planar such that flexible substrate 36 includes an array of electrodes 38 that all lie in the same plane on the same surface. In other examples, electrodes 38 may be positioned on different surfaces of flexible substrate 36 or set such that electrodes 38 lie within multiple planes. Additionally or alternatively, electrodes 38 may be positioned within multiple planes by, for example, bending or twisting flexible substrate 36 or slitting portions of flexible substrate 36 to form multiple flaps that can be bent or twisted into independent shapes each containing one or more electrodes 38.

In some examples, electrodes 38 may be arranged with a sufficient amount of separation between adjacent electrodes (e.g., separated by a distance in a range of about 10 mm to about 20 mm), to stimulate a relatively large treatment area. Such configurations may be useful for therapeutic treatments designed to stimulate treatment regions of patient 6 such as for the treatment of epilepsy. In another example, electrodes 38 may be arranged in a relatively narrow array (e.g., separated by a distance in a range of about 1.5 mm to about 3 mm), which may be useful for therapeutic treatments that may benefit from a larger degree of precision at the stimulated treatment site of patient 6. The individual electrodes 38 may be of any suitable size that define a suitable contact surface including, for example, circular, oval, rounded, square, rectangular, or the like that define a contact surface area of about 6 $mm^2$.

Electrode modules 34 may be detachable from primary hub 32. In particular, electrode modules 34 may detachably connect to primary hub 32. For example, primary hub 32, first electrode module 34a, and second electrode module 34b may be supplied as separate components that are assembled by the clinician during implantation of modular electrode assembly 30 in patient 6. Such examples may allow the clinician greater versatility to select the size, shape, and electrode configuration of electrode modules 34 best suited for a particular 6. For example, electrode modules 34 may be selected from a kit of modules that have many different sizes, number of electrodes 38, and/or arrangement of electrodes 38. Such examples may also allow the clinician greater versatility to tailor the first electrode module 34a and second electrode module 34b to apply different types of stimulation, for example, where the treatment may benefit from implanting non-identical electrode modules 34. This may further allow the clinician to determine whether one or both of electrode modules 34 are needed to treat the patient. In some scenarios, the clinician may elect to only use one or the other of electrode modules 34a or 34b. In other examples, electrode modules 34 may fixedly connect to primary hub 32. In such examples, electrode modules 34 may be attached to primary hub 32, e.g., during surgery or pre-surgery preparation, but be fixed and not readily detachable from primary hub 32 after attachment using, for example, interference fittings, unidirectional set screws, interlocking geometries, or the like.

Electrical connectors 44 and electrical contacts 40 may take on any suitable configuration that allows electrode modules 34 to be detachably coupled to primary hub 32. For example, electrical contacts 44 may include an electromechanical interface including, for example, a setscrew/setscrew block, a Bal Seal® terminal, a spring-loaded terminal, an interference fit terminal, or combinations thereof, or the like. In some examples, electrical connectors 44 and electrical contacts 40 may include corresponding spring clips (e.g., as described in FIGS. 4A-4C). Electrical connectors 44 and plurality of electrical contacts 40 may be made from any conductive material suitable to be implanted in patient 6.

In some examples, modular electrode assembly 30 may include one or more mechanical fasteners (e.g., set screws—not shown) to help physically secure the respective electrode modules 34 to primary hub 32. The mechanical fasteners may prevent the respective electrode modules 34 from becoming inadvertently disassembled during implantation and use of modular electrode assembly 30. In the case of set screws, for example, an electrical connector 44 may be inserted into an electrical contact 40, or vice versa, and a screw may be tightened to hold the coupled connection in place. Alternatively, a retainer clip may hold electrode modules 34 together with primary hub 32 and thereby maintain the coupling between connectors 44 and respective contacts 40. In some examples, electrode modules 34 and primary hub 32 may include complementary geometric structures (e.g., as described below) which may allow of electrode modules 34 to be secured to primary hub 32 without the inclusion of additional fasteners or using a reduced number of mechanical fasteners. As a further alternative, each electrical contact 40 may include a spring-biased terminal that is biased open by insertion of the electrical connector 44 and then biased against the connector to retain it in a recess formed by the contact 40. The male-female coupling arrangement of electrical connector 44 and electrical contact 40 may be inverted in other examples.

In some examples, the modular aspect of modular electrode assembly 30 may help reduce the amount of materials implanted in patient 6. For example, the modular aspect of modular electrode assembly 30 may significantly reduce the size of the body of lead 10 (e.g., by reducing the number of lead wires implanted), thereby reducing the size of elements that travel through the neck of patient 6 and along the scalp of patient 6 in order to supply electrical simulation to various target treatment sites in the brain 16, thereby increasing patient comfort and/or cosmetic appeal.

Modular electrode assembly 30 may be controlled by IMD 4 as shown in FIG. 1. In some examples, IMD 4 may be implanted within a subcutaneous pocket in a clavicle region of patient 6. Signals from IMD 4 may be transmitted to modular electrode assembly 30 by lead 10. In some examples, lead 10 may include a single lead or a bundle of multiple leads grouped together. For example, lead 10 may be a single lead that has a plurality of electrical conductors and corresponding distal electrodes (distal electrical contacts 23 of FIG. 2) (e.g., 2, 4, 8, 16, etc. conductors and electrodes) configured to supply electrical signals to each of the respective electrodes 38 of the electrode modules 34 (e.g., via the internal circuitry and contacts/connectors of primary hub 32 and electrode modules 34). Lead 10 may couple to IMD 4 directly or via a corresponding lead extension. In other examples, lead 10 may include more than one lead (e.g., a pair of leads), each including a plurality of electrical conductors (e.g., 8 conductors each) in each lead couples to IMD 4 directly or via a respective lead extensions. One lead may include conductors configured to supply electrical signal to each of the respective electrodes 38 of first detachable electrode module 34a and the other lead may include conductors configured to supply electrical signals to each of the respective electrodes 38 of second electrode module 34b. Lead 10, alone or with a lead extension, may define a length sufficient to traverse from IMD 4 to the target treatment site (e.g. about 75 mm to about 110 mm). While other examples are also contemplated by this disclosure, in some examples it may be useful to reduce the number of leads, e.g., to one lead or two leads, that travel from IMD 4 to modular electrode assembly 30 to reduce the amount of material implanted in patient 6 (e.g., reduce the number of leads to one or two leads). In some examples, the electrical conductors of a respective lead may run axially along the lead, while in other examples the electrical conductors may be wound in a coil that runs along the length of the respective lead.

Lead 10 may be implanted using a stylet for insertion stiffness while the lead 10 is implanted in the target tissue. For example, the stylet may allow a surgeon to easily manipulate lead 10 to guide the distal end of lead 10 from the clavicle region, though the neck, along the scalp, and into cranium 18 of patient 6. A stylet may also be used to lead 10 to other target tissues and other treatments, such as peripheral nerve stimulation (PNS), peripheral nerve field stimulation (PNFS), cortical stimulation (CS), pelvic floor stimulation, gastric stimulation, and the like. The stylet may be removable after insertion of lead 10 so that the stylet does not interfere with chronic treatment. In other examples, IMD 4 may be external to patient 6 with a percutaneous lead 10 connected between the stimulator and the modular electrode assembly 30 positioned at a target treatment site within the patient.

In some examples, lead 10 may be formed as part of or fixed to primary hub 32. For example, primary hub 32 may include embedded conductors (not shown) that extend from electrical contacts 40 through a primary hub 32 and one or more bodies of lead 10 along the scalp and neck of patient 6 to IMD 4 to supply electrical stimulation from IMD 4 to electrode modules 34. In other examples, primary hub 32 may be configured to couple to the distal end of one or lead 10. For example, primary hub may include a connector assembly (e.g., connector assembly 66 of FIG. 3A) that receives the distal end 21 of one or more leads 10 and facilitates the electrical coupling between the distal electrical contacts 23 of lead 10 and the internal circuitry of primary hub 32 (e.g., via conductors 88 of FIG. 4A).

In the example of FIG. 1, implantable IMD 4 may deliver electrical stimulation (e.g., cortical stimulation (CS)) therapy to patient 6 using electrodes 38 of modular electrode assembly 30 to treat any of a variety of neurological disorders or diseases. The stimulation may be delivered according to one or more programs executed by IMD 4 and configured to efficaciously treat a neurological condition in the brain of the patient, e.g. epilepsy.

Figure 2A:
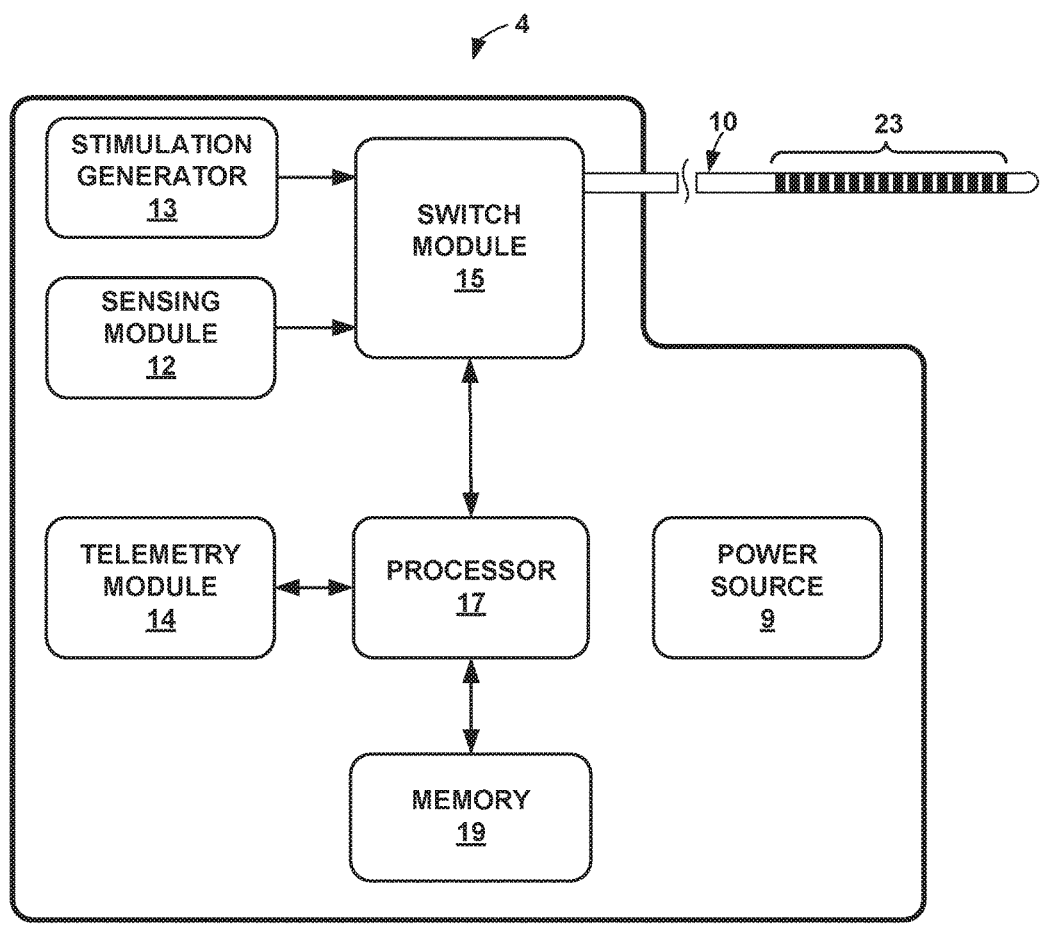
FIG. 2A is a conceptual diagram illustrating an example implantable medical device of FIG. 1.

FIG. 2A is a functional block diagram illustrating components of example IMD 4. In the example shown in FIG. 2A, IMD 4 includes memory 19, processor 17, stimulation generator 13, sensing module 12, switch module 15, telemetry module 14, and power source 9. Processor 17 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processor 17. The functions attributed to processors described herein, including processor 17, may be provided by a hardware device and embodied as software, firmware, hardware, or any combination thereof.

In some examples, IMD 4 may include sensing module 12 designed to sense bioelectrical brain signals of patient 6 by, for example, using one or more of electrode 38. The output of sensing module 12 may be received by processor 17. In some cases, processor 17 may apply additional processing to the bioelectrical signals, e.g., convert the output to digital values for processing and/or amplify the bioelectrical brain signal. In addition, in some examples, sensing module 12 or processor 17 may filter the signal from the selected electrodes 38 in order to remove undesirable artifacts from the signal, such as noise from cardiac signals generated within the body of patient 6. Although sensing module 12 is incorporated into a common outer housing with stimulation generator 13 and processor 17 in FIG. 2A, in other examples, sensing module 12 is in a separate outer housing from the outer housing of IMD 4 and communicates with processor 17 via wired or wireless communication techniques. In some examples, sensing module 12 may sense brain signals substantially at the same time that IMD 4 delivers therapy to patient 6. In other examples, sensing module 12 may sense brain signals and IMD 4 may deliver therapy at different times. Sensing module 12 may include electrical circuitry configured to perform the functions attributed to sensing module 12.

Memory 19 may include any volatile or non-volatile media, such as a random access memory (RAM), read only memory (ROM), non-volatile RAM (NVRAM), electrically erasable programmable ROM (EEPROM), flash memory, and the like. Memory 19 may store computer-readable instructions that, when executed by processor 17, cause IMD 4 to perform various functions described herein. Memory 19 may be considered, in some examples, a non-transitory computer-readable storage medium including instructions that cause one or more processors, such as, e.g., processor 17, to implement one or more of the example techniques described in this disclosure. The term "non-transitory" may indicate that the storage medium is not embodied in a carrier wave or a propagated signal. However, the term "non-transitory" should not be interpreted to mean that memory 19 is non-movable. As one example, memory 19 may be removed from IMD 4, and moved to another device. In certain examples, a non-transitory storage medium may store data that can, over time, change (e.g., in RAM).

In the example shown in FIG. 2A, processor 17 may control switch module 15 to sense bioelectrical brain signals with selected combinations of electrodes 38. In particular, switch module 15 may open or close electrical connections between sensing module 12 and selected electrodes 38 in order to selectively sense bioelectrical brain signals, e.g., in particular portions of brain 16 of patient 6. Processor 17 may also control switch module 15 to apply stimulation signals generated by stimulation generator 13 to selected combinations of electrodes 38. In particular, switch module 15 may couple stimulation signals to primary hub 32 via lead 10, which, in turn, delivers the stimulation signals to electrodes 38 via electrical contacts 44, electrical connectors 44, and electrical conductors 46. Switch module 15 may be a switch array, switch matrix, multiplexer, or any other type of switching module or electrical switching circuitry configured to selectively couple stimulation energy to selected electrodes 38 of electrode modules 34 and, in some examples, to selectively sense bioelectrical brain signals with selected electrodes 38. In some examples, however, IMD 4 does not include switch module 15. In some examples, IMD 4 may include separate voltage sources and sinks, or current sources and sinks, for each individual electrodes 38 (e.g., instead of a single stimulation generator) such that switch module 15 may not be necessary to direct electrical stimulation energy to selected electrodes. Instead, each electrode 38 may deliver current from its own current source and receive current that is directed to its own current sink. The current source and/or sink may be regulated or unregulated. Likewise, a voltage source and/or sink may be regulated or unregulated.

Stimulation generator 13 may be a single channel or multi-channel stimulation generator. For example, stimulation generator 13 may be capable of delivering, a single stimulation pulse, multiple stimulation pulses or a continuous signal at a given time via a single combination of two or more electrodes 38 or multiple stimulation pulses at a given time via multiple combinations of two or more electrodes 38. In some examples, however, stimulation generator 13 and switch module 15 may be configured to deliver multiple channels on a time-interleaved basis. For example, switch module 15 may serve to time divide the output of stimulation generator 13 across different combinations of electrodes 38 at different times to deliver multiple programs or channels of stimulation energy to patient 6.

Telemetry module 14 may support wireless communication between IMD 4 and an external programmer 20 or another computing device under the control of processor 17. Telemetry module 14 in IMD 4, as well as telemetry modules in other devices and systems described herein, such as programmer 20, may accomplish communication by radiofrequency (RF) communication techniques. In addition, telemetry module 14 may communicate with external programmer 20 via proximal inductive interaction of IMD 4 with programmer 20. Accordingly, telemetry module 14 may send information to external programmer 20 on a continuous basis, at periodic intervals, or upon request from IMD 4 or programmer 20. Telemetry module 14 may include electrical circuitry configured to perform the wireless telemetry described herein.

Power source 9 delivers operating power to various components of IMD 4. Power source 9 may include a small rechargeable or non-rechargeable battery and a power generation circuit to produce the operating power. Recharging may be accomplished through proximal inductive interaction between an external charger and an inductive charging coil within IMD 4. In some examples, power requirements may be small enough to allow IMD 4 to utilize patient motion and implement a kinetic energy-scavenging device to trickle charge a rechargeable battery. In other examples, traditional batteries may be used for a limited period of time.

In some examples, implantable IMD 4 delivers stimulation according to a group of programs at a given time. Each program of such a program group may include respective values for each of a plurality of therapy parameters, such as respective values for each of the intensity, pulse width (e.g., duration of a single stimulation), frequency, stimulation duration (e.g., duration in which a stimulation cycle is applied). Implantable IMD 4 may interleave pulses or other signals according to the different programs of a program group, e.g., cycle through the programs, to simultaneously treat different symptoms or different body regions, or provide a combined therapeutic effect. In such examples, programmer 20 may be used by a clinician to create programs, and assemble the programs into program groups.

Additionally, programmer 20 may be used by patient 6 to adjust stimulation parameters of one or more programs of a program group, and select a program group, e.g., from among a plurality of stored program groups, as the current program group to control delivery of stimulation by implantable IMD 4.

Figure 2B:
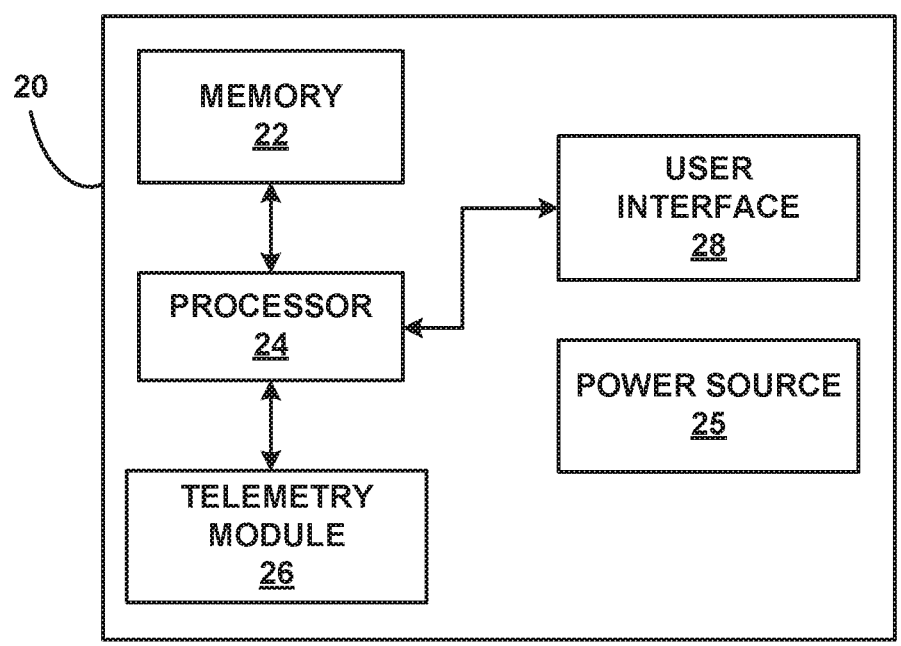
FIG. 2B is a conceptual diagram illustrating an example medical device programmer of FIG. 1.

FIG. 2B is a conceptual block diagram of an example external medical device programmer 20, which includes processor 24, memory 22, telemetry module 26, user interface 28, and power source 25. Processor 24 controls user interface 28 and telemetry module 26, and stores and retrieves information and instructions to and from memory 22. Programmer 20 may be configured for use as a clinician programmer or a patient programmer. Processor 24 may comprise any combination of one or more processors including one or more microprocessors, DSPs, ASICs, FPGAs, or other equivalent integrated or discrete logic circuitry, or any processing circuitry. Accordingly, processor 24 may include any suitable structure, whether in hardware, software, firmware, or any combination thereof, to perform the functions ascribed herein to processor 24.

Memory 22 may include instructions for operating user interface 28 and telemetry module 26, and for managing power source 25. Memory 22 may also store any therapy data retrieved from IMD 4 during the course of therapy. Memory 22 may include any volatile or nonvolatile memory, such as RAM, ROM, EEPROM or flash memory. Memory 22 may also include a removable memory portion that may be used to provide memory updates or increases in memory capacities. A removable memory may also allow sensitive patient data to be removed before programmer 20 is used by a different patient.

Memory 22 may be considered, in some examples, a non-transitory computer-readable storage medium including instructions that cause one or more processors, such as, e.g., processor 24, to implement one or more of the example techniques described in this disclosure. The term "non-transitory" may indicate that the storage medium is not embodied in a carrier wave or a propagated signal. However, the term "non-transitory" should not be interpreted to mean that memory 22 is non-movable. As one example, memory 22 may be removed from programmer 20, and moved to another device. In certain examples, a non-transitory storage medium may store data that can, over time, change (e.g., in RAM).

Wireless telemetry in programmer 20 may be accomplished by RF communication or proximal inductive interaction of external programmer 20 with IMD 4. This wireless communication is possible through the use of telemetry module 26. Accordingly, telemetry module 26 may be similar to the telemetry module contained within IMD 4. Programmer 20 also may be capable of infrared communication or direct communication through a wired connection. In this manner, other external devices may be capable of communicating with programmer 20 without needing to establish a secure wireless connection.

Power source 25 may deliver operating power to the components of programmer 20. Power source 25 may include a battery and a power generation circuit to produce the operating power. In some examples, the battery may be rechargeable to allow extended operation.

Figure 3A:
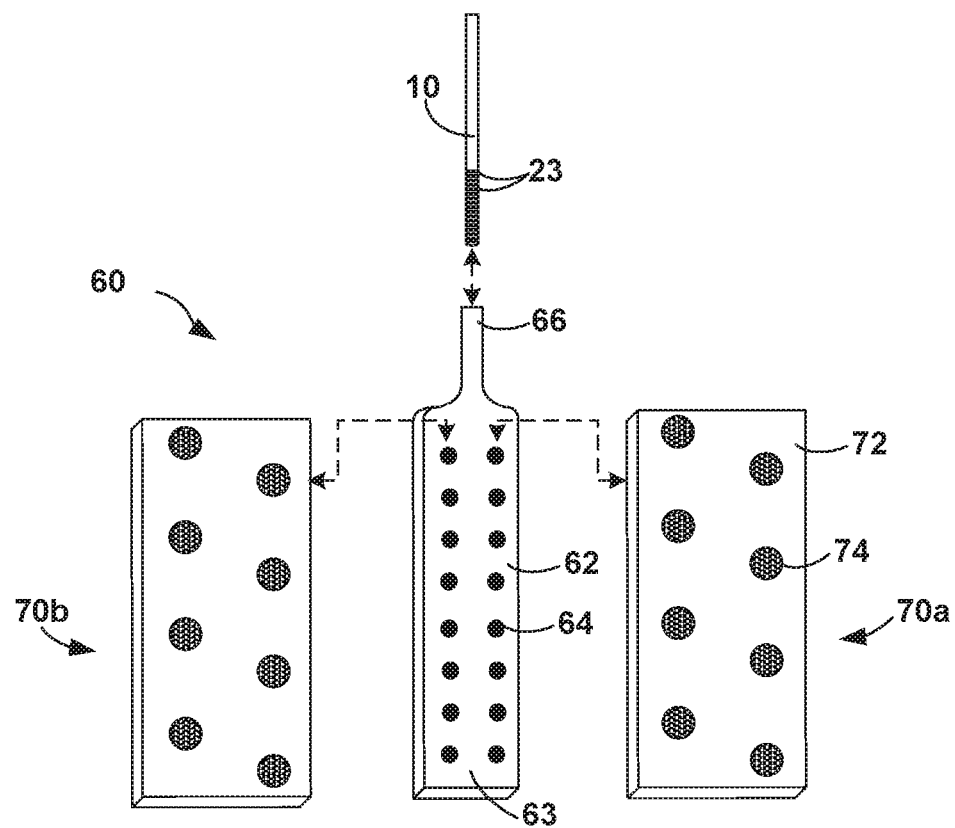
FIG. 3A is a conceptual diagram illustrating a bottom view of another example modular electrode assembly.
Figure 3B:
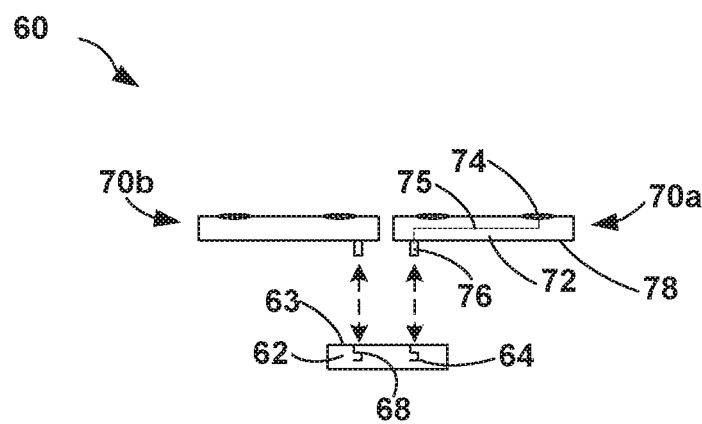
FIG. 3B is a conceptual diagram illustrating a front view of the example modular electrode assembly of FIG. 3A.

FIGS. 3A and 3B are conceptual diagrams illustrating another example modular electrode assembly 60 (e.g., bottom view (FIG. 3A) and front view (FIG. 3B)) that may be used to deliver neurological stimulation therapy to patient 6. Modular electrode assembly 60 may be similar to modular electrode assembly 30 of FIG. 1. Modular electrode assembly 60 includes a primary hub 62 that includes connector assembly 66 configured to receive lead 10 (e.g., couple to the distal electrical contacts 23 of lead 10) and transmit electrical signals received from lead 10 to electrical contacts 68 (FIG. 3B) disposed within a plurality of connective ports 64 arranged along a hub major surface 63. Primary hub 62 may include electrical contacts (not shown) configured to electrically couple to respective electrodes of the distal electrical contacts 23 of lead 10.

Primary hub 62 may be configured to receive a first electrode module 70a and a second electrode module 70b (collectively "electrode modules 70"). For example, electrode modules 70 may each include a flexible substrate 72 that defines a surface (e.g., major surface 78 (FIG. 3B)) that includes a plurality of electrical connectors 76 (FIG. 3B). Plurality of connective ports 64 may be arranged along hub major surface 63 in such a way that plurality of connective ports 64 receive corresponding electrical connectors 76 of first electrode module 70a and a second electrode module 70b.

Electrode modules 70 may each include a flexible substrate 72 that includes a plurality of electrodes 74 configured to deliver electrical stimulation to target treatment areas within patient 6 (e.g., the brain 16 or spinal cord of patient 6). The electrical stimulation may be transmitted from electrical connectors 76 to respective electrodes 74 using one or more electrical conductors 75 embedded in flexible substrate 72. In some examples, plurality of electrical connectors 76 and plurality of electrodes 74 may be positioned on opposite surfaces of flexible substrate 72 as shown in FIG. 3B such that electrode modules 70 may be implanted in patient 6 with electrodes 74 in contact with the target treatment areas followed by the installation of primary hub 62 electrode modules 70 so that hub major surface 63 face the target treatment site (e.g., brain 16) with electrode modules 70 positioned in between primary hub 62 and the target treatment site. In another example, plurality of electrical connectors 76 and plurality of electrodes 74 may be positioned on adjacent surfaces (e.g., as shown in FIG. 1) such that the major surfaces of the primary hub and electrode modules are positioned in direct contact with the treatment site with electrodes 74 receiving electrical impulses form IMD 4 (e.g., signal transmitted through the internal circuitry of hub 62, electrical contacts 68, electrical connectors 76 and internal circuitry, such as electrical conductors 75, of electrode modules 70). In such examples, the primary hub may also include one or more electrodes (not shown) configured to provide additional stimulation to the target treatment area. In another example, plurality of electrical connectors 76 and plurality of electrodes 74 may be positioned on the same surface of flexible substrate 72. In some examples, one or more of the electrode modules 70 may have electrodes 74 disposed on one or more of the surfaces of respective flexible substrates 72.

Figure 4A:
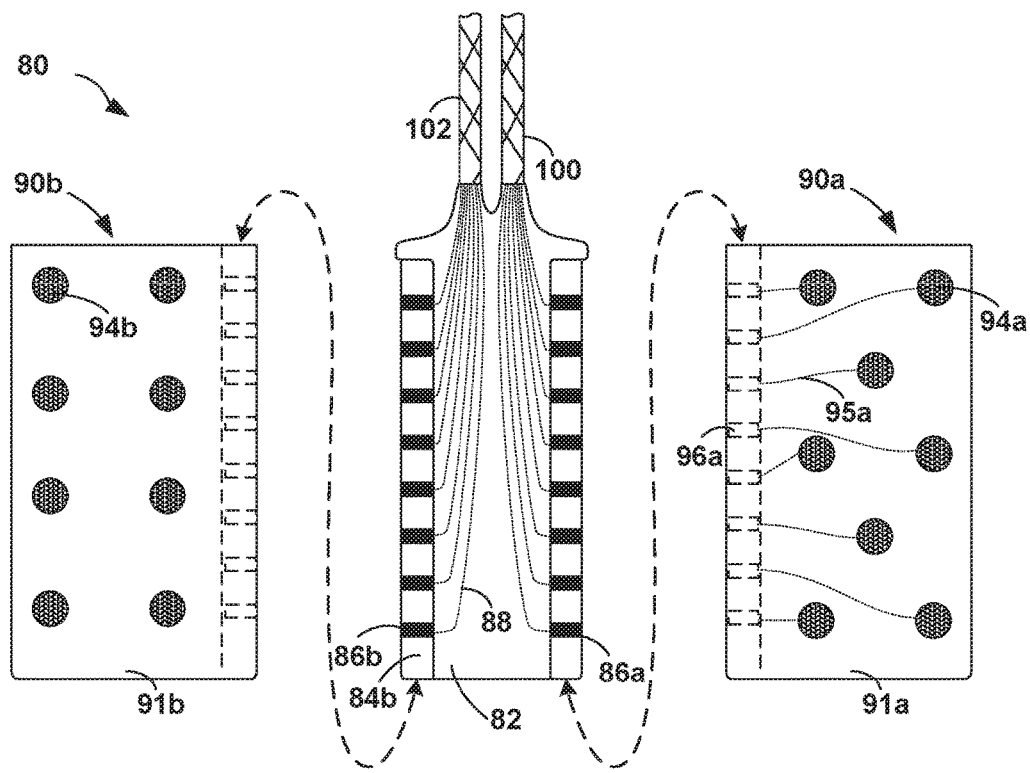
FIG. 4A is a conceptual diagram illustrating a bottom view of another example modular electrode assembly.
Figure 4B:
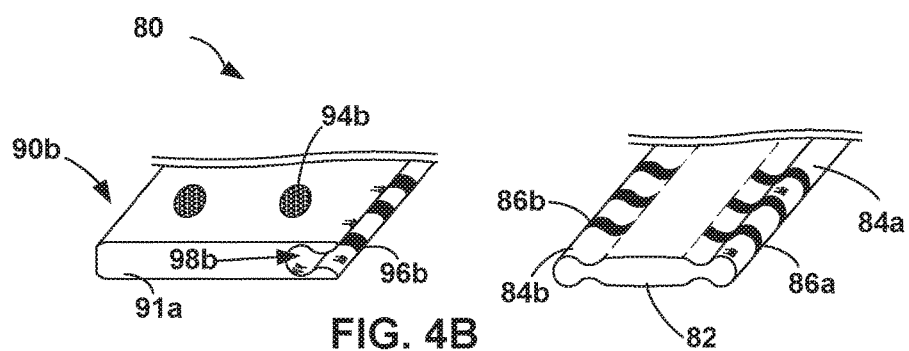
FIG. 4B is a conceptual diagram illustrating a perspective view of the example modular electrode assembly of FIG. 4A.
Figure 4C:
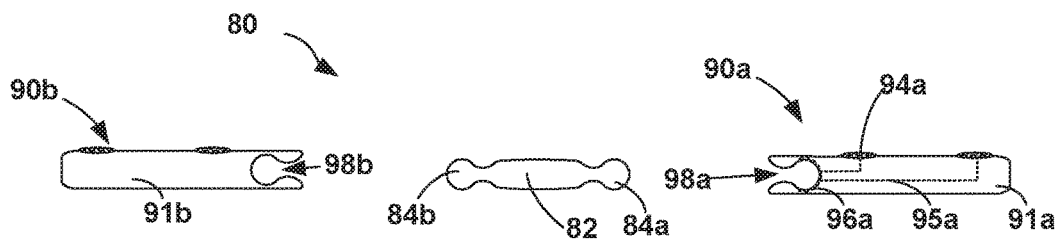
FIG. 4C is a conceptual diagram illustrating a front view of the example modular electrode assembly of FIG. 4A.

FIGS. 4A-4C are conceptual diagrams (e.g., bottom view (FIG. 4A), perspective view (FIG. 4B), and front view (FIG. 4C)) illustrating another example modular electrode assembly 80 that may be used to deliver neurological stimulation therapy to patient 6. Modular electrode assembly 80 includes a primary hub 82, first electrode module 90a, and second electrode module 90b. Each respective electrode module 90a, 90b may each include a flexible substrate 91a, 91b including a plurality of electrodes 94a, 94b (collectively "electrodes 94") disposed on one or more surfaces of respective flexible substrate 91a, 91b. Primary hub 82 may be configured to receive a pair of electrical leads 100 and 102 that make up a lead assembly (e.g. lead 10 of FIG. 1). In some examples, leads 100 and 102 deliver electrical stimulation from IMD 4 to a respective electrode module 90a, 90b. For example, primary hub 82 may include a plurality of conductors 88 configured to transmit electrical signals from proximal electrical contacts of leads 100 and 102 to a plurality of distal electrical contacts 86*a*, 86*b* of hub 82. In some examples, leads 100 and 102 may include a braided lead body to provide improved resistance to kinking and/or to mitigate possible conductor fractures in the respective lead.

In some examples, primary hub 82 may define one or more rails 84*a*, 84*b* that extend along a perimeter of primary hub 82. Electrode modules 90*a*, 90*b* may each include a respective slot 98*a*, 98*b* configured with a complementary geometry to receive one of rails 84*a*, 84*b* of primary hub 82. Each rail (e.g., rail 84*b*) may include a plurality of electrical contacts 86*b* disposed on an outer surface of rail 84*b* that may be configured to transmit electrical signals to respective electrodes 94*b*. For example, slot 98*b* may include corresponding electrical connectors 96*b* (e.g., spring clips or the like) within the slot 98*b* configured to pair and electrically communicate with respective electrical contacts 86*b*.

Electrical signals provided by IMD 4 may be transmitted through primary hub 82 via embedded circuitry 88 to a respective electrode module (e.g., electrode module 90*a*) by electrical contacts 86*a* on rail 84*a* to electrical connectors 96*a* of slot 98*a* and to a corresponding electrode 94*a* through one or more electrical conductors 95*a* embedded in flexible substrate 91*a* of the respective electrode module 90*a*. In some examples, rails 84*a*, 84*b* and slots 98*a*, 98*b* may take on a cylindrical shape with electrical contacts 86*a*, 86*b* and connectors 96*a*, 96*b* resembling C-shaped clips configured to overlap once electrode modules 90*a*, 90*b* are assembled to primary hub 82.

Figure 5A:
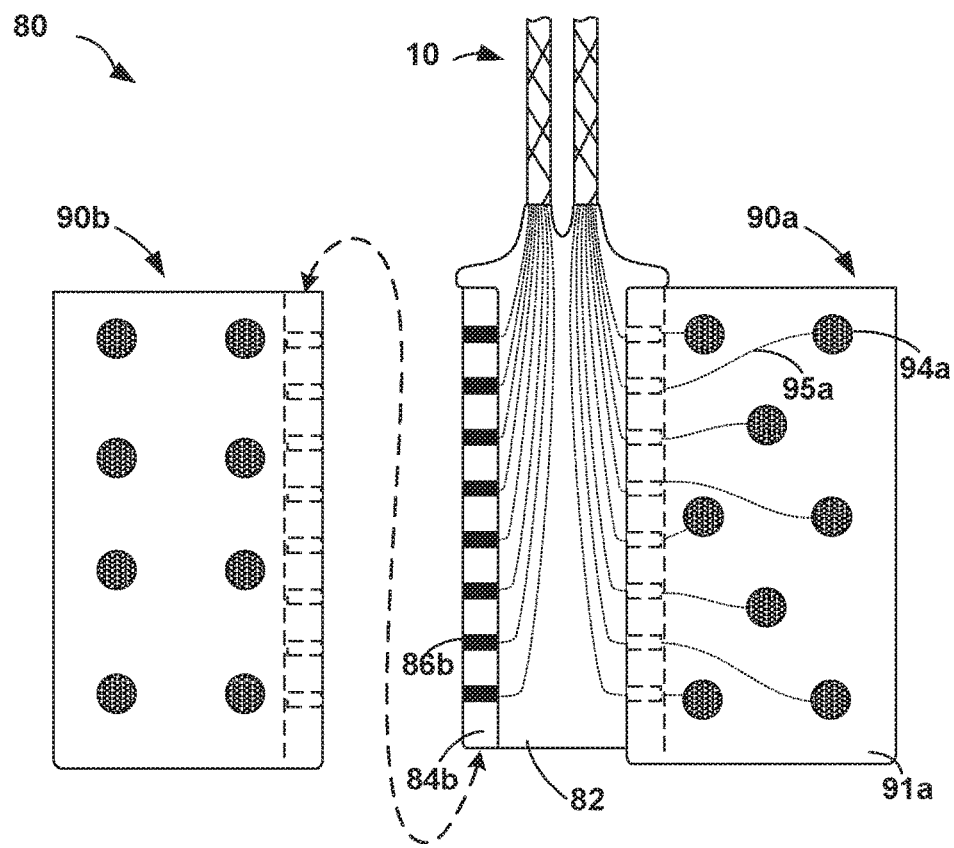
FIG. 5A is a conceptual diagram illustrating a bottom view of the example modular electrode assembly of FIG. 4A partially assembled.
Figure 5B:
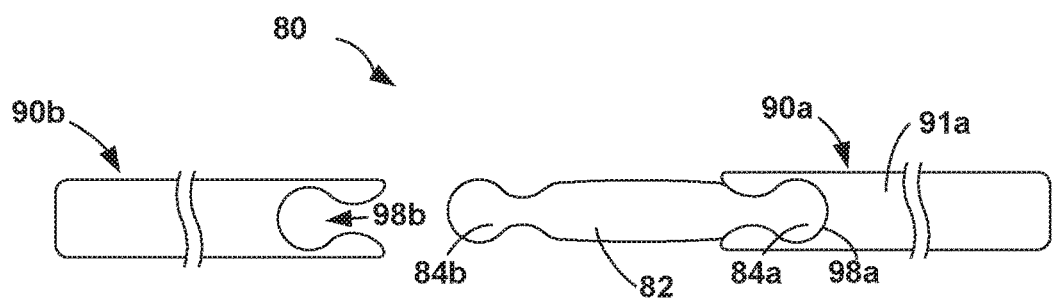
FIG. 5B is a conceptual diagram illustrating a front view of the example modular electrode assembly of FIG. 4A partially assembled.

In some examples, electrode modules 90*a*, 90*b* may be connected to primary hub 82 by slidably advancing a corresponding rail (e.g., rail 84*a*) of primary hub 82 in and along slot 98*a* of the corresponding electrode module 90*a* or, for example, by forcing rail 84*a* into the inner confines of slot 98*a* (e.g., click-connect in which slot 98*a* partially expands radially to receive rail 84*a*) such that re corresponding electrical contacts 86*a* align with a corresponding electrical connector 96*a*. For example, FIGS. 5A and 5B show respective bottom and front views of modular electrode assembly 80 where first electrode module 90*a* is connected to a corresponding rail 84*a* of primary hub 82 by slot 98*a*.

In some examples, rails 84*a*, 84*b* and slots 98*a*, 98*b* may exhibit complementing geometries such that rails 84*a*, 84*b* may be received by slots 98*a*, 98*b* and physically retained within slots 98*a*, 98*b*. Example geometries include a dog-bone like the structure as shown in FIGS. 4C and 5B, however other geometries are also envisioned. In some examples, rails 84*a*, 84*b* may also include one or more ribs, bumps, recesses, or the like (not shown) with reciprocal features in corresponding slots 98*a*, 98*b* to help promote alignment between electrode modules 90*a*, 90*b* and primary hub 82. In some examples the complementing geometries between rails 84*a*, 84*b* and slots 98*a*, 98*b* may allow the physician to attach and detach electrode modules 90*a*, 90*b* to primary hub 82 more than once to ensure appropriate fit and implantation of assembly 80 in patient 6.

Figure 6A:
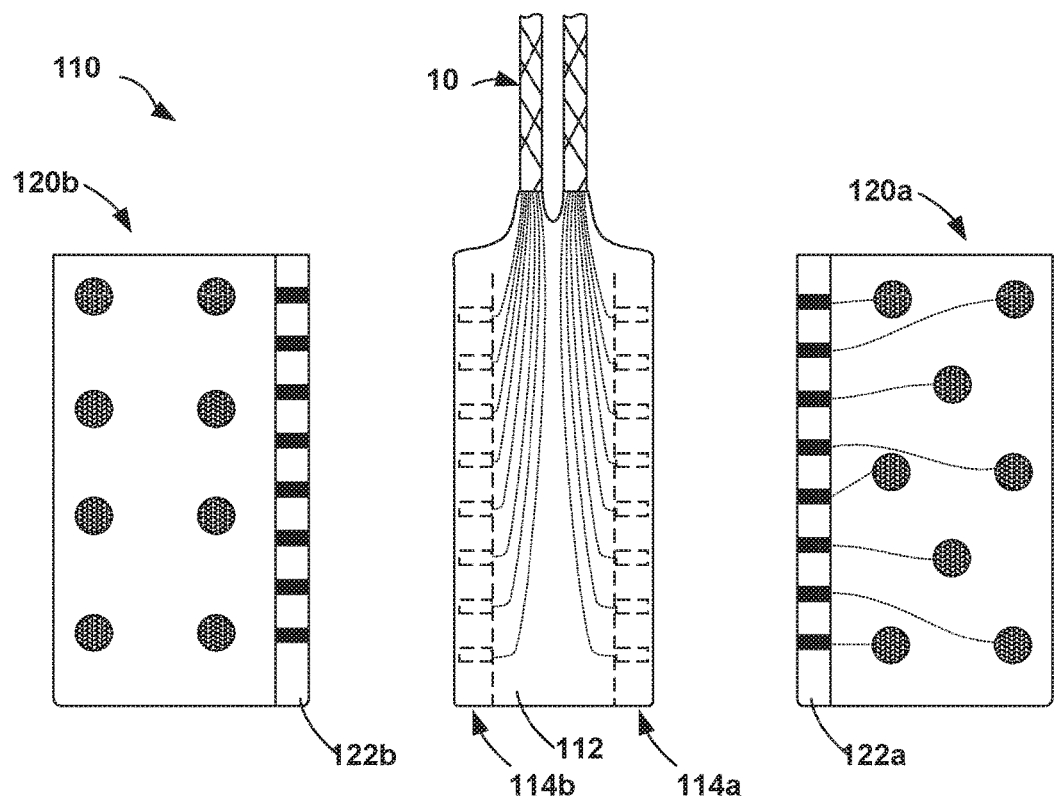
FIG. 6A is a conceptual diagram illustrating a bottom view of another example modular electrode assembly.
Figure 6B:
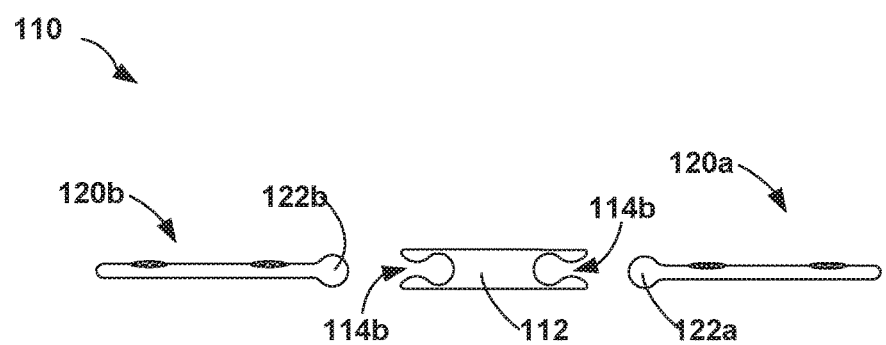
FIG. 6B is a conceptual diagram illustrating a front view of the example modular electrode assembly of FIG. 6A.

In some examples, the positioning of the respective rails 84*a*, 84*b* and slots 98*a*, 98*b* may be reversed with respect to primary hub 82 and electrode modules 90*a*, 90*b*. For example, FIGS. 6A-6B are conceptual diagrams (e.g., bottom view (FIG. 6A) and front view (FIG. 6B)) illustrating another example modular electrode assembly 110 that may be used to deliver neurological stimulation therapy to patient 6. Modular electrode assembly 110 includes a primary hub 112 that includes a pair of slots 114*a*, 114*b* extending along a perimeter of hub 112 and a first electrode module 120*a* and second electrode module 120*b*. Electrode modules 120*a*, 120*b* may each include a respective rail 122*a*, 122*b* along a perimeter of the module configured to be received within a corresponding slot 114*a*, 114*b* of primary hub 112. In some examples, primary hub 112 may include both rails (e.g., rail 84*a*) and slots (e.g, slot 114*b*).

Figure 7A:
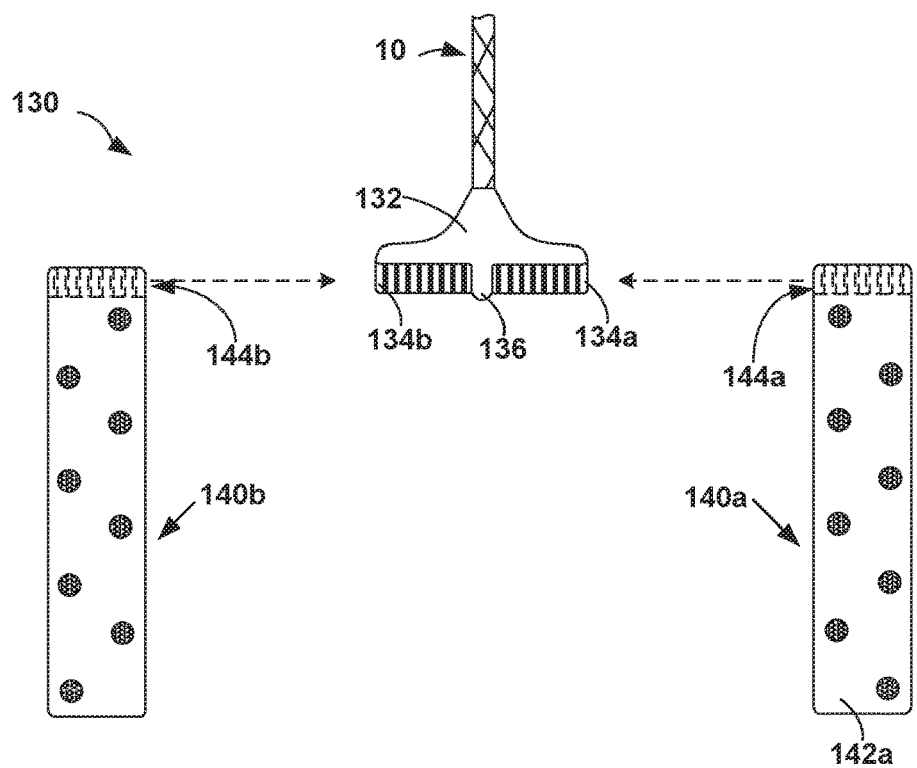
FIG. 7A is a conceptual diagram illustrating a bottom view of another example modular electrode assembly.
Figure 7B:
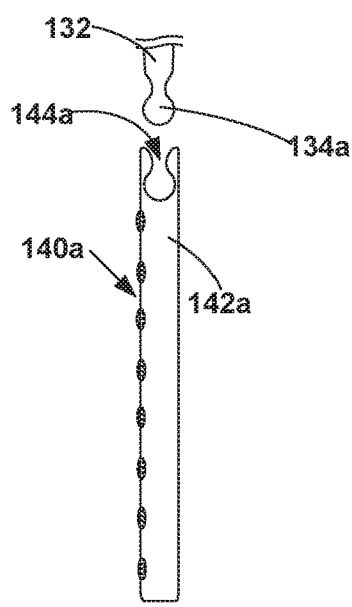
FIG. 7B is a conceptual diagram illustrating a side view of the example modular electrode assembly of FIG. 7A.

The rails or slots may be positioned in any suitable arrangement on the primary hub. For example, FIG. 5A shows rails 84*a*, 84*b* placed substantially parallel (e.g., parallel or nearly parallel) to one another. In some examples, the respective rails may be formed as a monorail that is segmented to receive multiple electrode modules (e.g., the central axes of each respective rail substantially aligned to form a single axis). For example, FIGS. 7A-7B are conceptual diagrams (e.g., bottom view (FIG. 7A) and side view (FIG. 7B)) illustrating another example modular electrode assembly 130 that may be used to deliver neurological stimulation therapy to patient 6. Modular electrode assembly 130 includes a primary hub 132 that includes a pair of rails 134*a*, 134*b* positioned in a monorail arrangement and extending along a perimeter of hub 132. Modular electrode assembly 130 also includes a first electrode module 140*a* and second electrode module 140*b* that each include a respective slot 144*a*, 144*b* that extends along a perimeter of the module and configure receive a corresponding rail 134*a*, 134*b* of primary hub 112. In such examples, primary hub 132 may also include a divider 136 that separates and helps distinguish the two rails 134*a*, 134*b* to aid in the assembly of modular electrode assembly 130.

Figure 8:
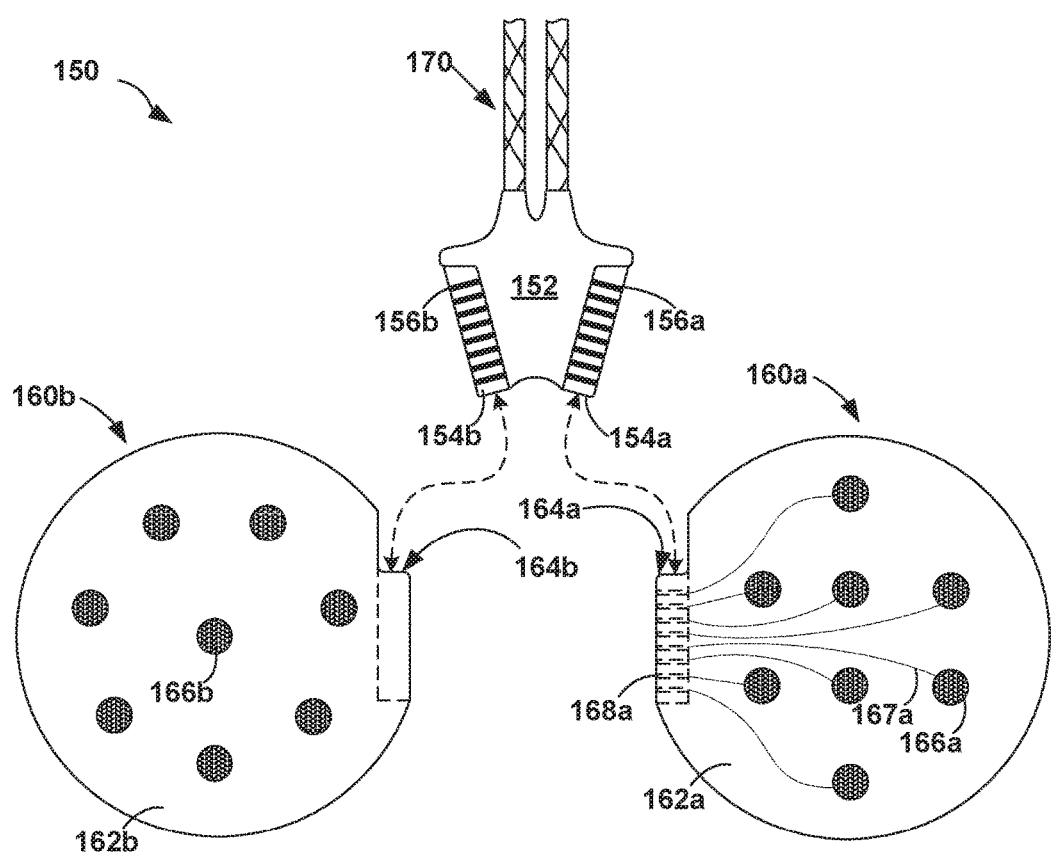
FIG. 8 is a conceptual diagram illustrating a bottom view of another example modular electrode assembly.

FIG. 8 is conceptual diagrams illustrating another example modular electrode assembly 150 that includes rails 154*a*, 154*b* in a non-parallel arrangement. Modular electrode assembly 150 includes a primary hub 152, first electrode module 160*a*, and second electrode module 160*b*. Electrode modules 160*a*, 160*b* may each include a flexible substrate 162*a*, 162*b* defining a semi-circular or paddled shape that includes a plurality of electrodes 166*a*, 166*b* disposed on one or more surfaces of respective flexible substrate 162*a*, 162*b*. Primary hub 152 may define pair rails 154*a*, 154*b* that extend along a perimeter of primary hub 152 wherein rails 154*a*, 154*b* and positioned in a non-parallel arrangement. Electrode modules 160*a*, 160*b* may each include a respective slot 164*a*, 164*b* configured to complement and receive a corresponding rail 154*a*, 154*b* of primary hub 152. Each rail 154*a*, 154*b* may include a plurality of electrical contacts 156*a*, 156*b* disposed on an outer surface of respective rail 154*a*, 154*b* that may be configured to transmit electrical signals from lead body 170 to respective electrodes 166*a*, 166*b*. For example, slot 164*a* may include corresponding electrical connectors 168*a* within the slot configured to pair and electrically communicate with a respective electrical contacts 156*a*. Electrical signals may be transmitted from electrical connectors 168*a* to a corresponding electrode 166*a* through one or more electrical conductors 167*a* embedded in flexible substrate 162*a*. While rails 154*a*, 154*b* are shown as substantially linear (e.g., the central axis of respective rail 154*a*, 154*b* forms a straight line), in some examples, rails 154*a*, 154*b* may be curvilinear.

While FIG. 8 depicts rails 154*a*, 154*b* as being substantially co-planar such that when electrode modules 160*a*, 160*b* are respectively attached to a corresponding rail, each major surface of first electrode module 160*a* is substantially co-planar with a corresponding major surface of second electrode module 160*b*, this need not be the case. For example, rails 154*a* and 154*b* and corresponding slots 164*a*, 164*b* could be configured so that once connected, the corresponding major surfaces of electrode modules 160a, 160b (e.g., surfaces including electrodes 166) define an angle less than 180 degrees there between the surfaces such that the corresponding major surfaces of electrode modules 160a 160b are not co-planar with one another. In some examples, the rails 154a and 154b and corresponding slots 164a, 164b may be sized to allow a certain degree of pivoting (e.g., a few degrees) between primary hub 152 and a respective electrode module 160a, 160b about the co-axis between the rail (e.g., rail 154a) and slot (e.g., slot 164a) such as a hinge. In some such examples, the maneuverabily may allow a clinician a greater of freedom in pairing modular electrode assembly 150 to the contours of the patient 6.

Figure 9:
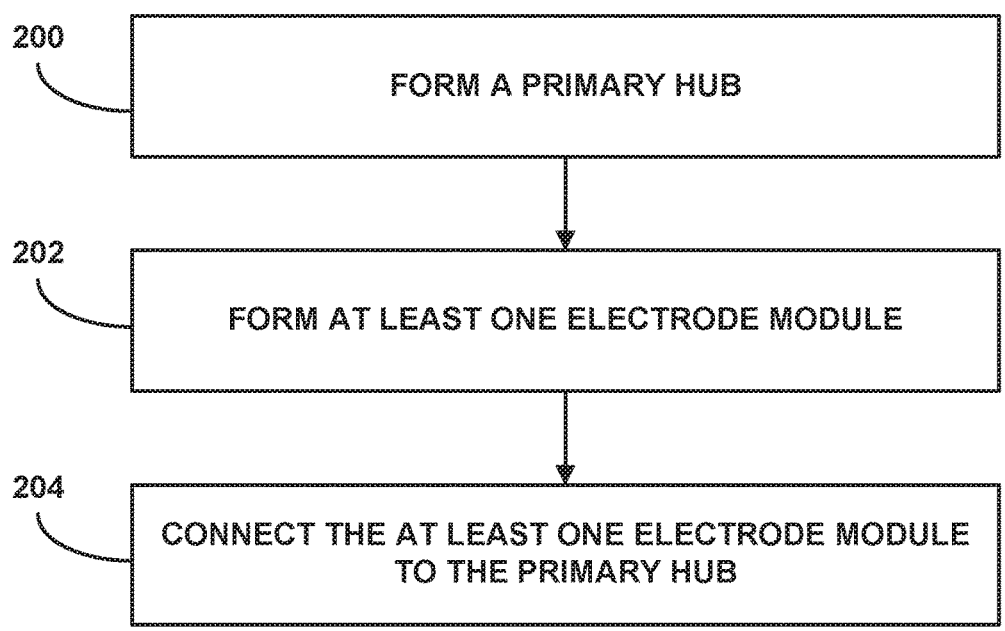
FIG. 9 is a flow diagram illustrating an example technique to form a modular electrode assembly.

The modular electrode assemblies of the invention may be formed using any suitable technique. FIG. 9 is a flow diagram illustrating an example technique for forming example modular electrode assembly accordance with the disclosure, such as, for example modular electrode assembly 80. While the technique shown in FIG. 9 is described with respect to modular electrode assembly 80, in other examples, the techniques may be used to form other modular electrode assemblies or portions of modular electrode assemblies that include different configurations or the modular electrode assemblies or portions of modular electrode assemblies described herein may be formed using techniques other than those described in FIG. 9.

The technique illustrated in FIG. 9 includes forming a primary hub 82 (200). As described above, primary hub 82 may be constructed using semi-flexibly substrate including, for example, silicone, polyurethane, or the like. The substrate may be molded or machined to form the various geometric features describe above (e.g., rails 84a, 84b or convective ports). The various electrical components of primary hub 82 (e.g., electrical contacts 86a, 86b and conductors 88) may be positioned and integrally added during the formation of the semi-flexibly substrate (e.g., as part of the fabrication process) or may be added after primary hub 82 is substantially formed. In some examples, primary hub 82 may also include a multiplexing device (not shown) to allow more than one electrical contact 86a, 86b of primary hub 82 to be powered by a single conductor of either leads 100 or 102 (e.g., distal electrical contacts 23 of lead 10).

The technique illustrated in FIG. 9 also includes forming at least one electrode module 90a (202). Electrode modules 90a, 90b may be formed of a flexible substrate 91a, 91b including, for example, silicone, polyurethane, or the like. The substrate 91a, 91b may be molded and/or machined (e.g., rolled) to exhibit a sufficient thickness to allow the electrode modules 90a, 90b to be implanted in patient 6. The substrate may also be shaped (e.g., molded, etched, etc.) to include complementing geometric slots 98a, 98b configured to received and electrically pair with rails 84a, 84b. The various electrical components of electrode modules 90a, 90b (e.g., electrical connectors 96a, 96b, conductors 95a, 95b, and electrodes 94a, 94b) may be integrally included with the formation of flexible substrate 91a, 91b (e.g., as part of the fabrication and/or molding process) or may be added electrode modules 90a, 90b is substantially formed (e.g., electrical connectors 96a may be introduced after slot 98a has been formed).

The technique illustrated in FIG. 9 also includes connecting the at least one electrode module (e.g., first electrode module 90a) to primary hub 82 (204). As discussed above, plurality of electrical connectors 96a and plurality of electrical contacts 86a may take on any suitable configuration that allows electrode modules 90a, 90b to be detachably coupled to primary hub 82. For example, electrical contacts 86a and electrical connectors 96a may include an electromechanical interface including, for example, a setscrew/setscrew block, a Bal Seal®, a spring clip, combinations thereof, or the like that allow primary hub 82 and electrode modules 90a, 90b to physically engage with one another to connect electrode modules 90a, 90b to primary hub 82. In some examples, primary hub 82 and electrode modules 90a, 90b may be connected using a rail and slot (e.g., rail 84a and slot 98a) configuration. For example, primary hub 82 may include one or more rails 84a, 84b and electrode modules 90a, 90b may include a corresponding slots 98a, 98b (or vice versa). First electrode modules 90a may be connected primary hub 82 by slidably advancing a corresponding rail 84a of primary hub 82 in and along slot 98a of the corresponding electrode module 90a or, for example, by forcing rail 84a into the inner confines of slot 98a (e.g., click-connect) such that electrical contacts 86a align with a corresponding electrical connector 96a. In some examples, connecting the at least one electrode module (e.g., first electrode module 90a) to primary hub 82 (214) may be done by the clinician at the time the modular electrode assembly 80 is implanted in patient 6.

Modular electrode assemblies described in this disclosure may be used in a variety of configurations for a variety of therapeutic applications. For example, a modular electrode assembly as described in this disclosure may be used to provide electrical stimulation therapy to a tissue site. Tissue sites may include any of a variety of organs, nerves, nerve bundles or nerve branches. The target tissue site may include, for example, organs such as the brain, heart, bladder, stomach, or sexual organs, and nerves, nerve bundles and nerve branches such as the spinal cord, gastric nerves, pelvic nerves, and peripheral nerves.

The stimulation may be, for example, deep brain stimulation (DBS), pelvic floor stimulation, gastric stimulation, spinal cord stimulation (SCS) or peripheral nerve stimulation. The stimulation may be configured to address any of a variety of symptoms or disorders such as Parkinson's Disease, essential tremor, or other movement disorders, epilepsy, obsessive compulsive disorder, or other neurological disorders, gastroparesis, obesity, pain, urinary or fecal dysfunction, or sexual dysfunction. Although various examples focus on cortical stimulation, the techniques of this disclosure may be applicable to any of a wide variety of different of types of electrical stimulation.

The techniques of this disclosure may be implemented in a wide variety of computing devices, medical devices, or any combination thereof. Any of the described units, modules or components may be implemented together or separately as discrete but interoperable logic devices or other electronic circuitry. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

Various examples have been described. These and other examples are within the scope of the following claims.

What is claimed is:

1. An implantable modular electrode assembly comprising:
   a hub comprising:
      a plurality of electrical contacts; and
      a hub substrate defining a plurality of ports, wherein each port of the plurality of ports comprises a respective electrical contact of the plurality of electrical contacts, and wherein the hub is configured to receive electrical signals from an implantable medical device;
   a first electrode module comprising:
      a first substrate;
      a first plurality of electrodes on the first substrate; and
      a plurality of electrical connectors on a surface of the first substrate, wherein each electrical connector of the plurality of electrical connectors is configured to be received by a respective port of the plurality of ports to connect the first electrode module to the hub, wherein at least some of the plurality of electrical contacts electrically communicate with the first plurality of electrodes; and
   a second electrode module comprising a second substrate and a second plurality of electrodes on the second substrate, wherein the second electrode module is connectable to the hub, wherein at least some of the plurality of electrical contacts electrically communicate with the second plurality of electrodes.

2. The implantable modular electrode assembly of claim 1, wherein the plurality of electrical connectors on a surface of the first substrate comprises a first plurality of electrical connectors on a surface of the first substrate, wherein the second electrode module comprises a second plurality of electrical connectors on a surface of the second substrate, wherein each electrical connector of the second plurality of electrical connectors is configured to be received by a respective port of the plurality of ports to connect the second electrode module to the hub.

3. The implantable modular electrode assembly of claim 1, wherein the first plurality of electrodes form a first two-dimensional array on the surface of the first substrate.

4. The implantable modular electrode assembly of claim 3, wherein the second plurality of electrodes form a second two-dimensional array on the surface of the second substrate, wherein the first two-dimensional array and the second two-dimensional array form mirror images of one another.

5. The implantable modular electrode assembly of claim 3, wherein the second plurality of electrodes form a second two-dimensional array on the surface of the second substrate, wherein the first two-dimensional array is different than the second two-dimensional array.

6. The implantable modular electrode assembly of claim 1, wherein the hub comprises a connector assembly configured to receive a lead, wherein the lead includes conductors to transmit the electrical signals from the implantable medical device to the hub.

7. The implantable modular electrode assembly of claim 1, wherein the first substrate comprises a first flexible substrate and the second substrate comprises a second flexible substrate.

8. The implantable modular electrode assembly of claim 1, wherein the first electrode module is detachably coupled to the hub.

9. A system comprising:
   an implantable medical device;
   at least one lead electrically connected to the implantable medical device; and
   a modular electrode assembly electrically connected to at least one lead, the modular electrode assembly comprising:
      a hub comprising:
         a plurality of electrical contacts; and
         a hub substrate defining a plurality of ports, wherein each port of the plurality of ports comprises a respective electrical contact of the plurality of electrical contacts, and wherein the hub is configured to receive electrical signals from the implantable medical device;
      a first electrode module comprising:
         a first substrate;
         a first plurality of electrodes on the first substrate; and
         a plurality of electrical connectors on a surface of the first substrate, wherein each electrical connector of the plurality of electrical connectors is configured to be received by a respective port of the plurality of ports to connect the first electrode module to the hub, wherein at least some of the plurality of electrical contacts electrically communicate with the first plurality of electrodes; and
      a second electrode module comprising a second substrate and a second plurality of electrodes on the second substrate, wherein the second electrode module is connectable to the hub, wherein at least some of the plurality of electrical contacts electrically communicate with the second plurality of electrodes;
   wherein the implantable medical device is configured to transmit electrical signals through the lead to the first and second plurality of electrodes.

10. The system of claim 9, wherein the plurality of electrical connectors on a surface of the first substrate comprises a first plurality of electrical connectors on a surface of the first substrate, wherein the second electrode module comprises a second plurality of electrical connectors on a surface of the second substrate, wherein each electrical connector of the second plurality of electrical connectors is configured to be received by a respective port of the plurality of ports to connect the second electrode module to the hub.

11. The system of claim 9, wherein the first plurality of electrodes form a first two-dimensional array on the surface of the first substrate.

12. The system of claim 11, wherein the second plurality of electrodes form a second two-dimensional array on the surface of the second substrate, wherein the first two-dimensional array and the second two-dimensional array form mirror images of one another.

13. The system of claim 11, wherein the second plurality of electrodes form a second two-dimensional array on the surface of the second substrate, wherein the first two-dimensional array is different than the second two-dimensional array.

14. The system of claim 9, wherein the hub comprises a connector assembly configured to receive a lead, wherein the lead includes conductors to transmit the electrical signals from the implantable medical device to the hub.

15. The system of claim 9, wherein the first substrate comprises a first flexible substrate and the second substrate comprises a second flexible substrate.

16. The system of claim 9, wherein the first electrode module is detachably coupled to the hub.

* * * * *